United States Patent [19]
Munny

[11] 4,312,081
[45] Jan. 26, 1982

[54] PROSTHETIC JOINTS FOR CRURAL AMPUTEES

[76] Inventor: Günter Munny, Wipperfürther Str. 49, 5064 Odenthal-Eikamp, Fed. Rep. of Germany

[21] Appl. No.: 172,160

[22] Filed: Jul. 25, 1980

[30] Foreign Application Priority Data

May 19, 1980 [DE] Fed. Rep. of Germany ....... 3019048

[51] Int. Cl.³ .............................. A61F 1/04; A61F 1/08
[52] U.S. Cl. ........................................................... 3/22
[58] Field of Search ....................................... 3/21–29, 3/2

[56] References Cited

U.S. PATENT DOCUMENTS

| | | | |
|---|---|---|---|
| 2,046,069 | 6/1936 | Greissinger | 3/29 |
| 2,457,482 | 12/1948 | Marean | 3/29 |
| 3,597,767 | 8/1971 | Prahl | 3/22 X |
| 3,928,873 | 12/1975 | Zevering | 3/27 |
| 4,085,466 | 4/1978 | Goodfellow et al. | 3/22 X |

FOREIGN PATENT DOCUMENTS

| | | | |
|---|---|---|---|
| 828292 | 1/1952 | Fed. Rep. of Germany | 3/22 |
| 851394 | 10/1952 | Fed. Rep. of Germany | 3/2 |
| 978586 | 12/1964 | United Kingdom | 3/21 |

*Primary Examiner*—Ronald L. Frinks
*Attorney, Agent, or Firm*—McGlynn and Milton

[57] ABSTRACT

A prosthetic joint for crural amputees of the kind comprising a hollow shank, open at the top, for receiving a femoral stump and, articulated to this shank, an insertion member for fitment of a crural prosthesis, is provided with a sliding guide rigidly connected to the insertion member, a sliding member displaceable in the guide and having a lower plane surface and an upper arcuate surface, an arcuate slideway fixed to the rear of the under side of the shank to accommodate the arcuate surface of the sliding member and a pivotal link which connects the rear parts of the shank and the insertion member and effects a forward displacement of the sliding member upon pivotal movement of the insertion member relative to the shank.

9 Claims, 3 Drawing Figures

PROSTHETIC JOINTS FOR CRURAL AMPUTEES

This invention relates to a prosthetic joint for crural amputees, the joint comprising a hollow shank, open at the top, for receiving a femoral stump and articulated to this shank, an insertion member for fitment of a crural prosthesis.

The shank is made with the help of an impression taken of the intact femoral stump and is then, when in use, pushed over this stump to which it is then rigidly connected in known manner by means of securing straps or the like. In corresponding manner, a crural prosthesis made from wood, synthetic plastics material or other materials is attached to the insertion member.

Artificial joints hitherto used for these purposes are on the one hand completely of metal which means they are heavy and thus burdensome to wear. On the other hand, the known artificial joints have the disadvantage that when the lower leg formed by the prosthesis is bent, it can be clearly seen through the trouser leg that this part of the leg is artificial. In particular, when these known artificial joints are bent, sharp edges or projections protrude at the front at the place where the natural leg has the knee cap.

Accordingly, the invention is concerned with the problem of providing an improved prosthetic joint for crural amputees which does not have these disadvantages, which is, in other words, of low weight while being nevertheless rugged and in which no projections or sharp edges protrude at the front when the leg is bent.

According to the invention, this problem is resolved by providing the joint with a sliding guide rigidly connected to the insertion member, a sliding member displaceable in said guide and having a lower plane surface and an upper arcuate surface, an arcuate slideway fixed to the rear of the under side of the shank to accommodate the arcuate surface of the sliding member and a pivotal link which connects the rear parts of the shank and the insertion member and effects a forward displacement of the sliding member upon pivotal movement of the insertion member relative to the shank.

Therefore, this prosthetic joint is what may be referred to as a rotary-sliding joint. In other words, the arcuate slideway in conjunction with the arcuate surface of the sliding member not only produces a rotary or pivotal movement about a fixed axis but at the same time, the disposition of the link results in a forward displacement of the sliding member which is disposed between the shank with the arcuate slideway on the one hand and the insertion member with the plane slideway on the other. This simultaneous pivoting and displacement is inter alia, also brought about by locating the point of articulation of the upper end of the link to the shank behind the central point or centre line of the arcuate slideway. In consequence of this, in the event of movement along the arcuate slideway, this point of articulation of the upper end of the link is likewise moved along an arcuate path so that the link itself is compelled to pivot about its other point of articulation. This pivoting action in turn has the result that the entire rotary joint which consists of the arcuate slideway and the arcuate sliding face of the sliding member, is compelled to move forward. This forward movement is made possible by the sliding member being displaceable on the plane sliding guide of the insertion member. Preferably, when the crural prosthesis is vertical, the plane sliding guide is not exactly horizontal but is inclined upwards at a slight angle in a forward direction.

The expression "forward" used herein refers to that side of the prosthetic joint, the shank or the insertion member which is to the fore during walking movement, in other words, the side at which the knee cap is located in a natural leg.

For practical purposes, it is sufficient to provide one link on just one side of the artificial joint. It goes without saying that, if necessary, a second link may also be provided on the other side.

To prevent the insertion member carrying the crural prosthesis in the prosthetic joint from becoming detached from the shank and thus from the femoral stump any suitable retaining means may be employed. Preferably however, it is envisaged that the sliding guide should engage in substantially C-shaped fashion around both sides of the bottom part of the sliding member.

Correspondingly, it is envisaged that the sliding member should engage in substantially C-shaped fashion around both sides of the bottom of the slideway fixed to the shank. This surrounding and clamping fitment can of course also be arranged the other way round. In any event, it prevents the joint from falling apart in either the straight sliding guide or the circular sliding guide.

Preferably, it is envisaged that the sliding member and/or the sliding guide and/or the slideway should be made of materials having negligible friction, preferably a synthetic plastics material. In this case, it is then possible to dispense with special lubrication which would otherwise entail problems with regard to dirtying of the trouser leg.

In order to restrict pivoting movement of this prosthetic joint in the extended condition, an abutment is preferably fixed to the shank at the front end of the slideway. Furthermore, for limiting pivoting movement in the extended condition, a stop is provided at the rear end of the sliding guide, which stop is fixed to the insertion member and limits displacement of the sliding member in a rearward direction.

According to a further feature of the invention, an elastic band covers the front of the prosthetic joint and at the same time exerts a pull in the sense of extending the prosthetic joint, said elastic band being fixed at its upper end to the shank and at its lower end to the insertion member and covering a considerable length of these two parts, but above all covering the component parts of the prosthetic joint.

Furthermore, for lateral covering of the prosthetic joint, it is envisaged to provide plate-like projections which are disposed on the insertion member, on either side of the sliding guide, and which are integral with the insertion member, said projections engaging laterally over the bottom part of the shank.

The crural prosthesis can be connected to the insertion member in known manner. Preferably, for adjustable attachment, a retaining stud is provided which widens out conically in a downward direction and which, by means of known matching members, permits of a certain degree of orientation and adjustment of the crural prosthesis.

The invention will be described in greater detail hereinafter with reference to the embodiment shown in the accompanying drawings, in which.

Figure 1:
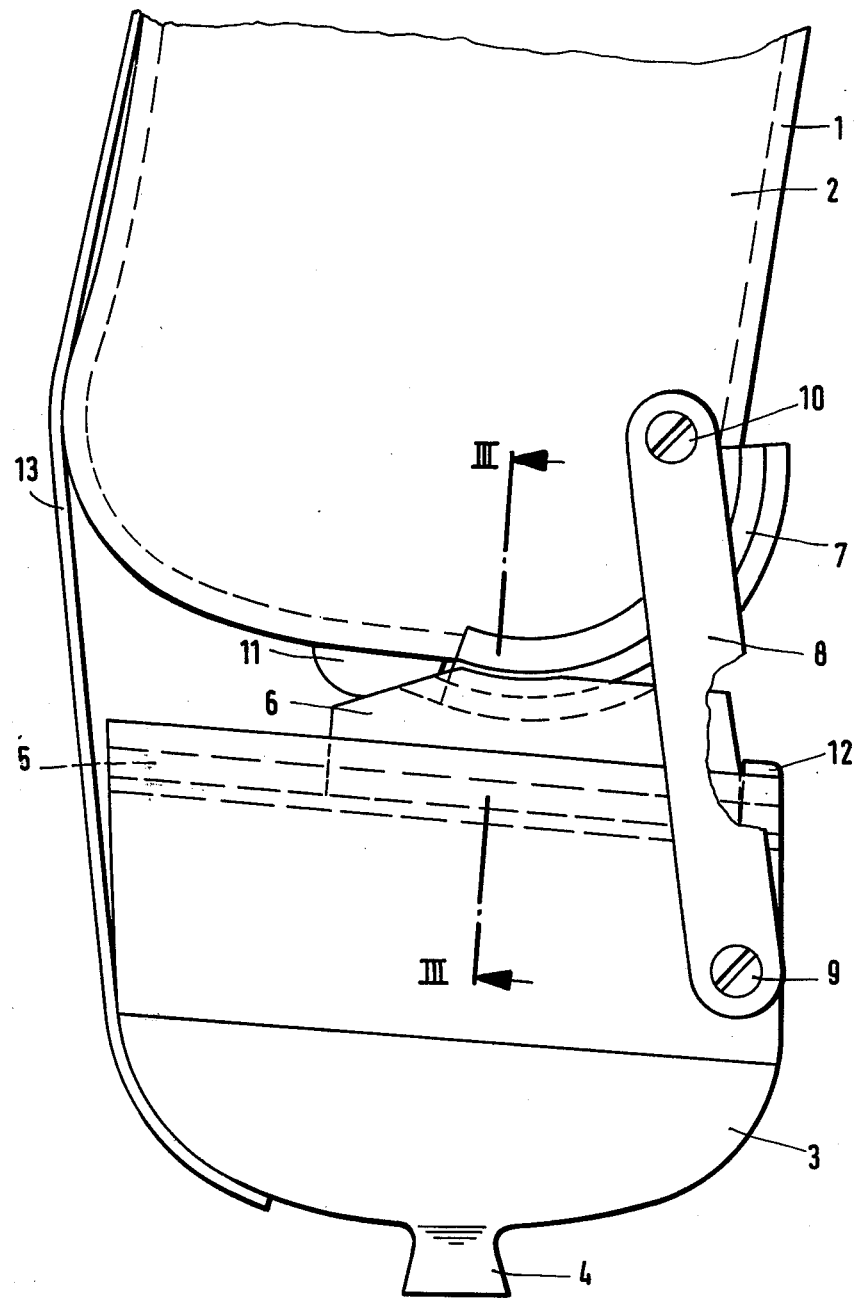
FIG. 1 is a side view of a prosthetic joint according to the invention, in the extended condition.

As can be seen from the drawings, the prosthetic joint includes a hollow shank 1 which is open at the top and which is pushed onto a femoral stump 2 being rigidly connected to the latter in known manner, by means not shown. The shank is made of synthetic plastics material and is prefabricated from an impression taken of the femoral stump.

The joint further includes an insertion member 3 which is stepped at the bottom and provided with a retaining stud 4 permitting of adjustable attachment of a crural prosthesis (not shown). The insertion member is, in the embodiment illustrated, also produced from synthetic plastics material.

Figure 3:
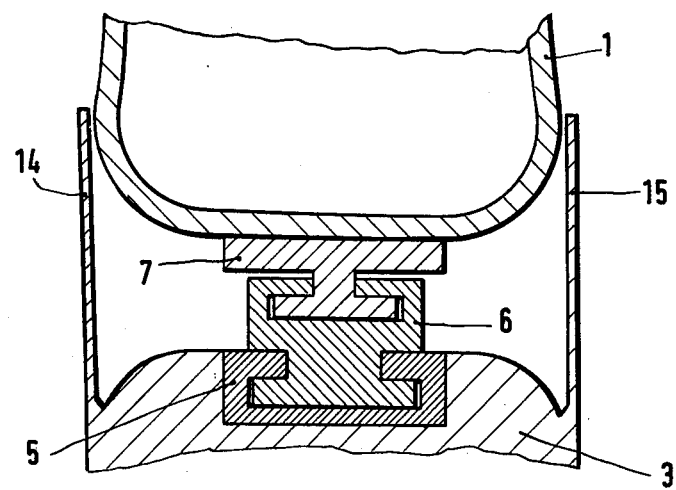
FIG. 3 is a section taken on the line III—III in FIG. 1.

The prosthetic joint further includes an articulating connection between the shank 1 and the insertion member 3. This articulating connection consists of a sliding guide rigidly connected to the insertion member 3, which guide has a plane slideway and is disposed to rise slightly in relation to the longitudinal axis of the prosthesis in the direction of the front of the joint. As can be seen in FIG. 3, this sliding guide 5 is let into the insertion member 3 and is substantially C-shaped. Slidably displaceable in this guide and likewise made of synthetic plastics material, is a member 6, the lower end of which is shaped to fit the sliding guide 5, while its upper end has a C-shaped recess. This recess is however, of arcuate form and accommodates an arcuate slideway 7 fixed to the rear part of the lower end of the shank 1, the said slideway 7 therefore, being held captive on the shank 1 while being displaceable relative to the sliding member 6 in the direction of the arc.

The joint is completed by a link 8 which is pivotally connected at 9 to the rear part of the insertion member 3 and at 10 to the rear part of the shank 1. By virtue of the fact that the pivotal point 10 on the shank 1 lies behind the centre point (not shown) of the arcuate slide path, when the joint is bent into the position shown in FIG. 2, the pivotal point 10 moves along an arc around the aforesaid centre point into the position shown in FIG. 2. However, since the pivotal point 10, by virtue of the constraint imposed by the link 8, also has to pivot about the lower pivotal point 9 of the link, it necessarily follows that a forward displacement of the shank in relation to the insertion member occurs.

This construction of the articulating connection as a rotary-sliding joint does however produce a very natural-looking pivoting movement and thus avoids the already described disadvantages of the known prosthetic joint. The displaced position of the shank 1 is denoted in FIG. 2 by the reference numeral 1', while that of the link 8 is denoted in FIG. 2 by the reference numeral 8'.

As shown in FIG. 3, plate-like projections 14 and 15 (not shown in FIGS. 1 and 2) extend from the member 3 on either side of the joint. These projections engage over the bottom part of the shank 1 and cover both sides of the joint. If desired, the plate-like projections can also be bent around somewhat forwardly.

The pivoting movement of the joint is, in the extended position shown in FIG. 1, limited by a projection 11 mounted on the bottom of the shank 1 and against which abuts a corresponding chamfered portion on the sliding member 6, the pivoting movement of the joint also being restricted by an abutment 12 fixed to the insertion member at the rear end of the sliding guide 5.

Figure 2:
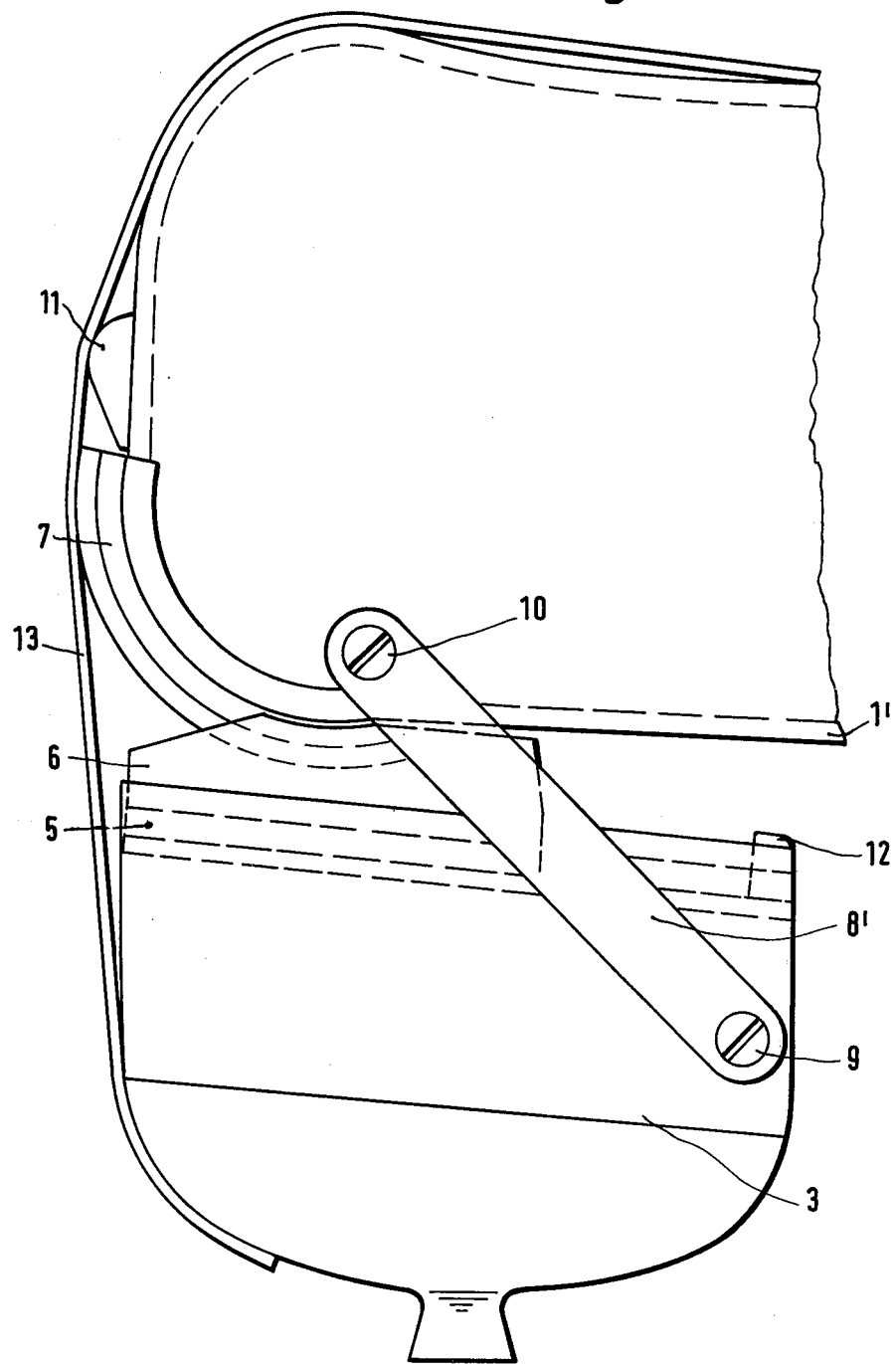
FIG. 2 is a side view of the prosthetic joint shown in FIG. 1 but in the bent condition.

In the bent condition of the joint, the side wall of the shank 1', as shown in FIG. 2, rests on the top of the rear part of the sliding member 6. Any further forward displacement of the sliding member 6 beyond the position shown in FIG. 2 is prevented by the link 8'.

At the front of the joint, the shank 1 and the insertion member 3 are joined by an elastic band 13 rigidly connected at its ends to the shank and to the insertion member respectively and covering the front of the gap between these two parts. Furthermore, in the bent condition, the band exerts a pull which seeks to stretch the prosthetic joint.

What is claimed is:

1. A prosthetic joint for crural amputees, comprising a hollow shank, open at the top, for receiving a femoral stump and, articulated to this shank, an insertion member for fitment of a crural prosthesis, characterized by a slide guide rigidly connected to the insertion member, a sliding member displaceable in said guide and having a lower plane surface and an upper arcuate surface, an arcuate slideway fixed to the rear part of the under side of the shank to accommodate the arcuate surface of the sliding member and a pivotal link which connects the rear parts of the shank and the insertion member and effects a forward displacement of the sliding member upon pivotal movement of the insertion member relative to the shank.

2. A prosthetic joint according to claim 1, characterised in that the slide guide engages in substantially C-shaped fashion around both sides of the lower part of the sliding member.

3. A prosthetic joint according to claim 1 or 2, characterised in that the sliding member engages in substantially C-shaped fashion around both sides of the lower part of the slideway fixed to the shank.

4. A prosthetic joint according to claim 1, characterised in that at least one of the sliding member, the slide guide and the slideway is made of a material having negligible friction, preferably a synthetic plastics material.

5. A prosthetic joint according to claim 1, characterised by an abutment fixed to the upper end of the slideway on the shank for limiting pivoting movement in the extended condition of the prosthetic joint.

6. A prosthetic joint according to claim 1, characterised by an abutment fixed to the rear end of the slide guide on the insertion member, for limiting the displacement of the sliding member in a rearward direction.

7. A prosthetic joint according to claim 1, characterised by an elastic band covering the front of the prosthetic joint and at the same time exerting a pull which seeks to extend the prosthetic joint, said elastic band being fixed at its upper end to the shank and at its lower end to the insertion member.

8. A prosthetic joint according to claim 1, characterised by plate-like projections which extend in one piece from the insertion member on both sides of the slide guide and engage over the lower part of the shank for laterally masking the prosthetic joint.

9. A prosthetic joint according to claim 1, characterised in that the insertion member has at its lower end, a downwardly conically widening retaining stud for the adjustable fitment of the crural prosthesis.

* * * * *